(12) United States Patent
Cardosi

(10) Patent No.: US 11,361,850 B1
(45) Date of Patent: Jun. 14, 2022

(54) HEALTHCARE SERVICE SYSTEM

(71) Applicant: Free Market Health LLC, Pittsburgh, PA (US)

(72) Inventor: Joseph Cardosi, Pittsburgh, PA (US)

(73) Assignee: Free Market Health, Inc., Pittsburgh, PA (US)

( * ) Notice: Subject to any disclaimer, the term of this patent is extended or adjusted under 35 U.S.C. 154(b) by 554 days.

(21) Appl. No.: 16/538,289

(22) Filed: Aug. 12, 2019

Related U.S. Application Data

(60) Provisional application No. 62/816,689, filed on Mar. 11, 2019, provisional application No. 62/815,967, filed on Mar. 8, 2019, provisional application No. 62/718,241, filed on Aug. 13, 2018.

(51) Int. Cl.
*G16H 10/60* (2018.01)
*G06Q 10/06* (2012.01)
*G06Q 30/08* (2012.01)

(52) U.S. Cl.
CPC ....... *G16H 10/60* (2018.01); *G06Q 10/06393* (2013.01); *G06Q 30/08* (2013.01)

(58) Field of Classification Search
CPC ........ G06Q 30/08; G06Q 40/08; G06Q 10/10; G06Q 30/0275; G16H 40/20
See application file for complete search history.

(56) References Cited

U.S. PATENT DOCUMENTS

2003/0195838 A1* 10/2003 Henley .............. G06Q 30/0212
                                                    705/37
2007/0250342 A1* 10/2007 Sohal ..................... G06Q 30/08
                                                    705/37

\* cited by examiner

*Primary Examiner* — Joseph D Burgess
(74) *Attorney, Agent, or Firm* — Gordon Rees Scully Mansukhani, LLP

(57) ABSTRACT

A healthcare service system including an intake and validation module, a patient stratification and bid criteria module, and a bidding platform. An order certification phase initiates including an incoming order taken from the intake module after verifying eligibility. The incoming order is then taken through the patient stratification and bid criteria module for evaluation and establishing value-driven requirements of the healthcare provider. After the order has been certified a bidding platform will take the order and manage the reverse auction. The healthcare order is then monitored for performance.

8 Claims, 8 Drawing Sheets

HEALTHCARE SERVICE SYSTEM

CROSS-REFERENCE TO RELATED APPLICATION

This application claims priority to and the benefit of the following U.S. Provisional Patent Application Nos. 62/718,241 (filed Aug. 13, 2018), 62/815,967 (filed Mar. 8, 2019), and 62/816,689 (filed Mar. 11, 2019) which are all incorporated by reference herein in its entirety.

BACKGROUND

The present disclosure relates generally to the technical field of online healthcare management and, in one specific example, to facilitating web-based, value-driven, reverse-auction style bidding among providers of various health care services. The systems and methods discussed throughout this application may pertain to the field of online healthcare management in general. Preferably, the systems and methods disclosed herein relate to the specialty pharmacy market.

The specialty pharmacy market is the fastest growing segment of the various drug channels in the United States. The majority of the share of the specialty pharmacy market is currently concentrated among only approximately four specialty pharmacies. Another ten percent of market share is spread across approximately the next six largest specialty pharmacies. The remaining twenty-five percent share is spread among thousands of other, smaller specialty pharmacies.

While the barrier to entry into the specialty pharmacy segment is quite low, a variety of market forces create a significant barrier to a pharmacy attempting to grow within this segment. This barrier to growth explains why seventy-five percent of the twenty-five million specialty prescriptions are serviced by only approximately ten specialty pharmacy companies. Key elements acting as growth barriers for the smaller pharmacies include: exclusive or limited-network payer contracts for specialty drug fulfillment, access to referrals, specialty pharmacy capabilities and sophistication, and access to specialty drugs. The pharmacies enjoying the largest market share have the scale and resources to invest within these elements, leading to a larger chasm between those with significant specialty pharmacy market share and those without. While there is size and scale within the large specialty pharmacies (which leads to continual market share protection), there's a void in transformative, value-based innovation within the business models of the specialty pharmacy market.

Although the number of specialty prescriptions and the number of servicing specialty pharmacies have both increased dramatically over the last decade, the specialty pharmacy referral acquisition, contracting, and prescription management processes, in general, has remained stagnant with minimal disruptive innovation. And while value-based payment and care models are increasingly common in today's healthcare market, they are not yet well-executed in the specialty pharmacy segment. The systems and methods disclosed in the present application aim to solve this problem.

SUMMARY

The present application discloses an embodiment for a system comprising a web-based reverse-auction style bidding system having one or more processors and a memory storing instructions that, when executed by the one or more processors, cause the one or more processors to perform various operations. These operations include, for example: detecting, by an order detector, a healthcare service order that is available to be fulfilled by a user; stratifying, by a data-informed patient stratifier establishing, by a bid criteria establishment unit, a bid criteria required to be accepted by the user; confirming, by an order certifier, that the healthcare service order is payable; identifying, by a bid manager, a minimum required bid assigned to the health care service order; determining, by a time frame manager, a predetermined bidding time frame during which a bid must be submitted by the user; and initiating, by an auction manager, a bidding process for a duration of the predetermined bidding time frame. The system is configured so that when the predetermined bidding time frame expires, the auction manager awards the health care service order to the user submitting the bid with a lowest monetary value.

The application also discloses a method that includes detecting, by an order detector, a healthcare service order that is available to be fulfilled by a service provider. The method also includes the step of stratifying, by a data-informed patient stratifier; determining, by a bid criteria detector, the type of performance metrics that will be measured of the service provider; establishing, by a bid criteria establishment unit, a bid criteria required to be accepted by the user; and confirming, by an order certifier, that the healthcare service order is payable. The method includes identifying, by a bid manager, a minimum required bid assigned to the health care service order; determining, by a time frame manager, a predetermined bidding time frame during which a bid must be submitted, and initiating, by an auction manager, a bidding process for a duration of the predetermined bidding time frame. According to the disclosed method, when the predetermined bidding time frame expires, the auction manager awards the health care service order to the user submitting the bid with a lowest monetary value.

It is to be understood that both the foregoing general description and the following detailed description are exemplary and explanatory only, and are not restrictive of the invention as claimed.

BRIEF DESCRIPTION OF THE DRAWINGS

Features, aspects, and advantages of the present disclosure will become apparent from the following description, appended claims, and the accompanying exemplary embodiments shown in the drawings, which are briefly described below.

DETAILED DESCRIPTION

Example methods and systems to provide a reverse-auction style bidding system that may be implemented in an online environment are described. In the following description, for purposes of explanation, numerous specific details are set forth in order to provide a thorough understanding of example embodiments. It will be evident, however, to one skilled in the art that the present invention may be practiced without these specific details. The various components and steps of the systems and methods described herein are depicted, in general, in FIG. 7, which shows an exemplary order certification phase, an exemplary competitive bidding phase, and an exemplary on-going performance metric evaluation phase for the specialty drug or pharmacy market.

A reverse-auction style bidding system for identifying a healthcare service order that is available to be fulfilled, certifying the healthcare service order as payable, initiating a bidding process, and awarding receipt of the health care service order to a lowest bidder is disclosed herein. A healthcare service order, preferably a specialty pharmacy order, is typically identified as available to be fulfilled when the bidding system receives a health care service order (e.g., a referral, prescription, etc.) from an outside entity. The outside entity may be, for example, an insurance company, a doctor or doctor's office, a pharmacy or specialty pharmacy, a drug or health care device manufacturer, or a specialty pharmacy hub vendor. The healthcare service order may be received by the bidding system via any method of manual or electronic means, including fax, email, and electronic prescribing.

Figure 1:
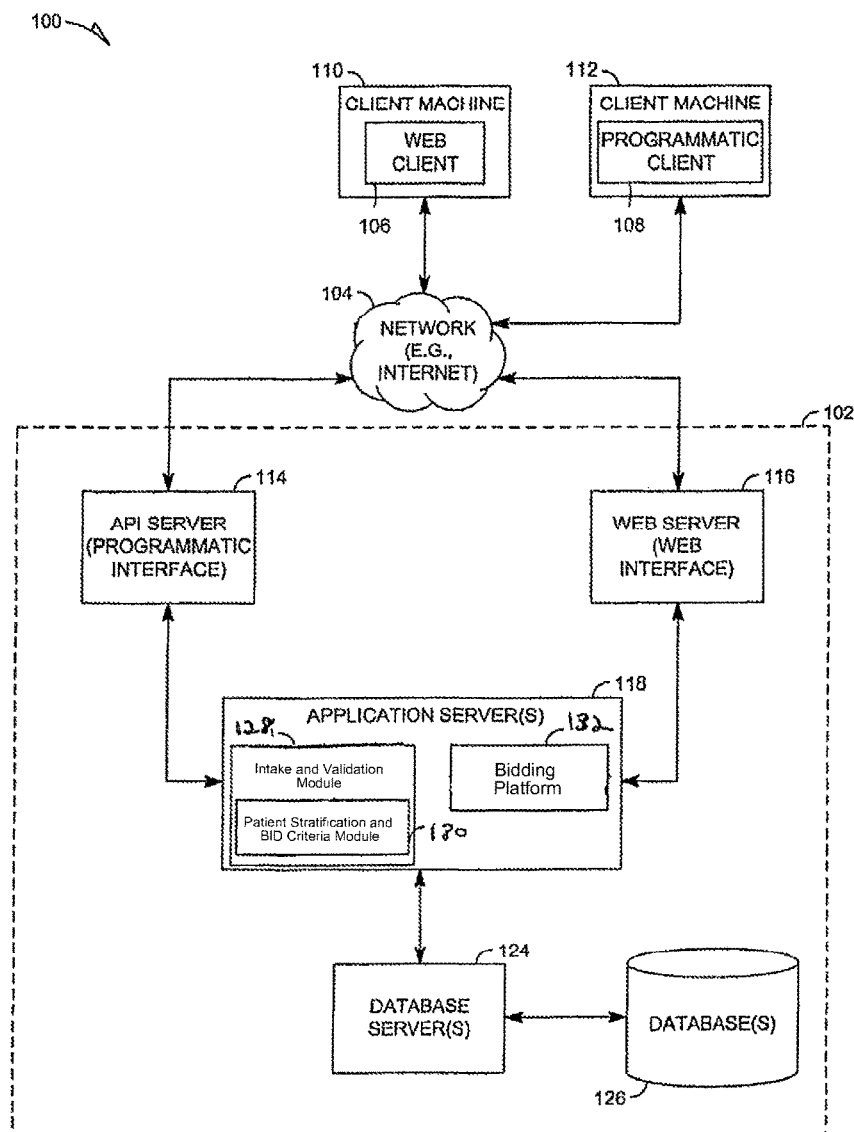
FIG. 1 is a network diagram depicting a client-server system, within which one example embodiment may be deployed.

Some disclosed embodiments may be implemented within a client-server system 100 as depicted in the network diagram of FIG. 1. FIG. 1 illustrates, for example, a web client 106 (e.g., a browser, such as the Internet Explorer browser developed by Microsoft Corporation of Redmond, Wash.), and a programmatic client 108 executing on respective client machines 110 and 112. An Application Program Interface (API) server 114 and a web server 116 are coupled to, and provide programmatic and web interfaces respectively to, one or more application servers 118. The application servers 118 host one or more applications 120. The application servers 118 are, in turn, shown to be coupled to one or more databases servers 122 that facilitate access to one or more databases 124.

Figure 7:
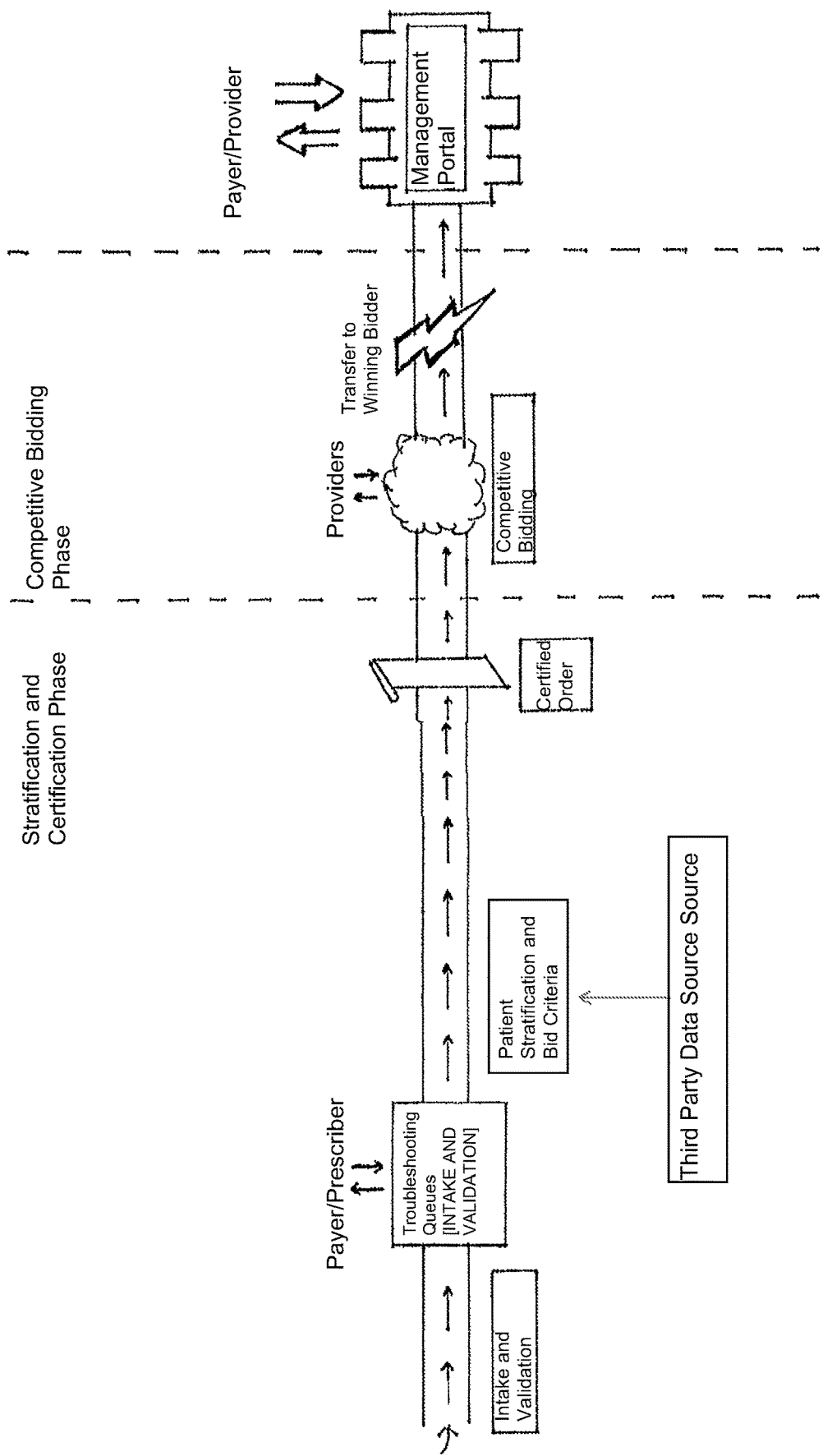
FIG. 7 illustrates one embodiment of the bidding system from intake through ongoing performance metric evaluation.

When a healthcare service order is identified as available for bidding, it is transmitted from an outside entity, as described above, and received and stored in the database(s) 126. As shown in FIGS. 2 and 7, intake and validation module 128 performs the steps of the intake and validation process, which is described in greater detail below in FIG. 3. When the intake and validation process is complete, the patient stratification and bid criteria module 130 then performs the steps of the patient stratification and bid criteria process, which is described in greater detail in FIG. 4. At this point in the process, the client or user is able to access the healthcare service order via the competitive bidding platform by logging into the competitive bidding platform using login credentials. The bidding platform then performs the steps of the bidding process, which is described in greater detail in FIG. 5. Once logged in, a client (e.g., a service provider) may access details about the healthcare service order and determine whether to participate in the competitive bidding process. In order to participate in the bidding process, the client must first agree to accept certain bid criteria, if applicable, for a specific healthcare service order, which is discussed in more detail below.

Figure 2A:
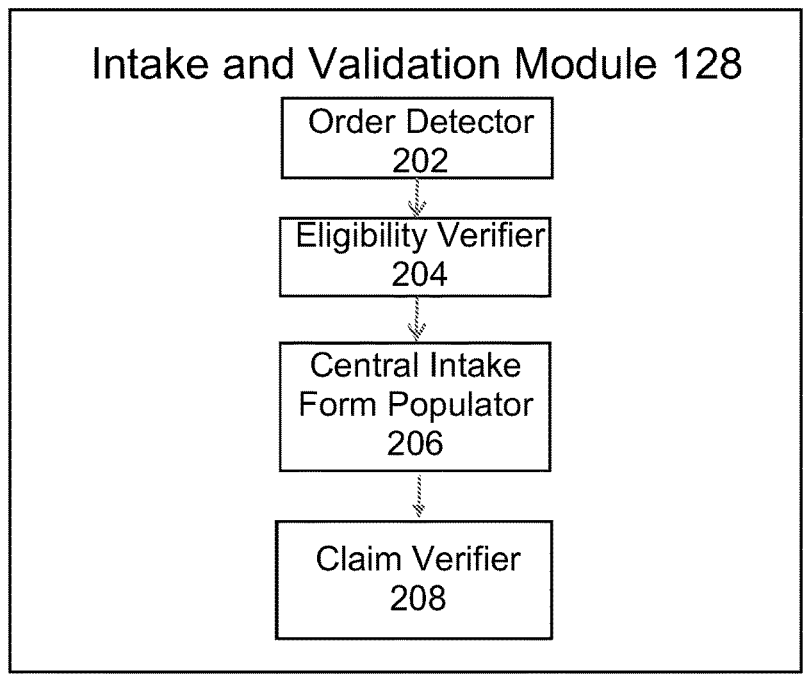
FIGS. 2A-2C are block diagrams depicting the intake and validation module, patient stratification and bid criteria module and bidding platform that are provided as part of one embodiment.
Figure 2B:
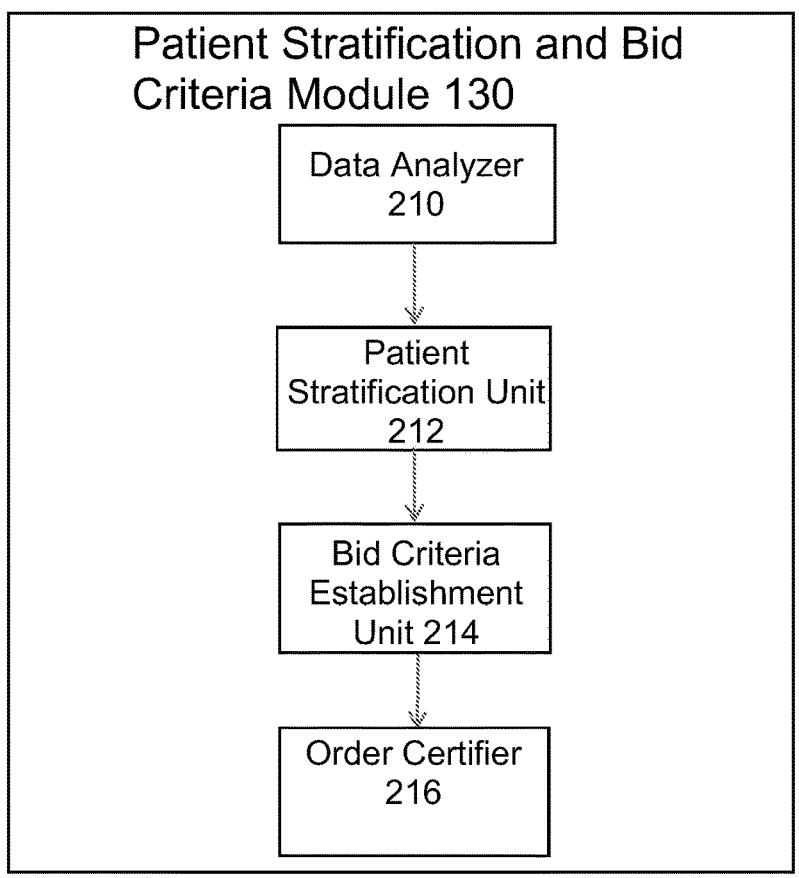
Figure 2C:
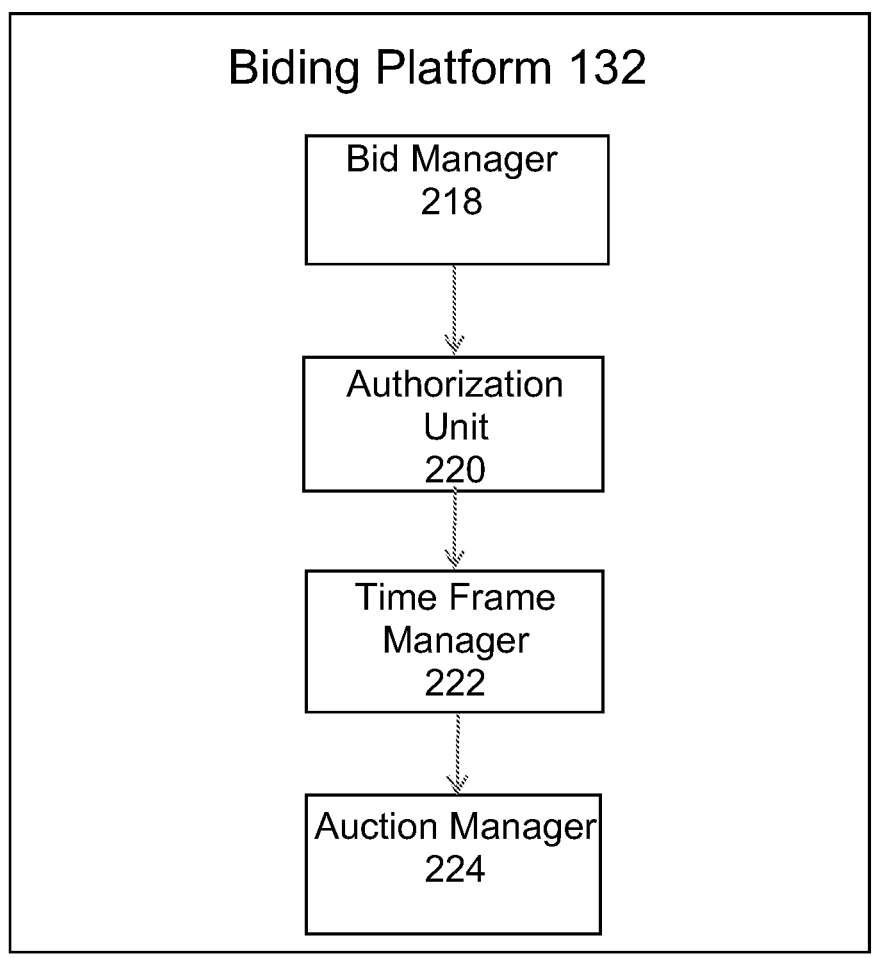
Figure 3:
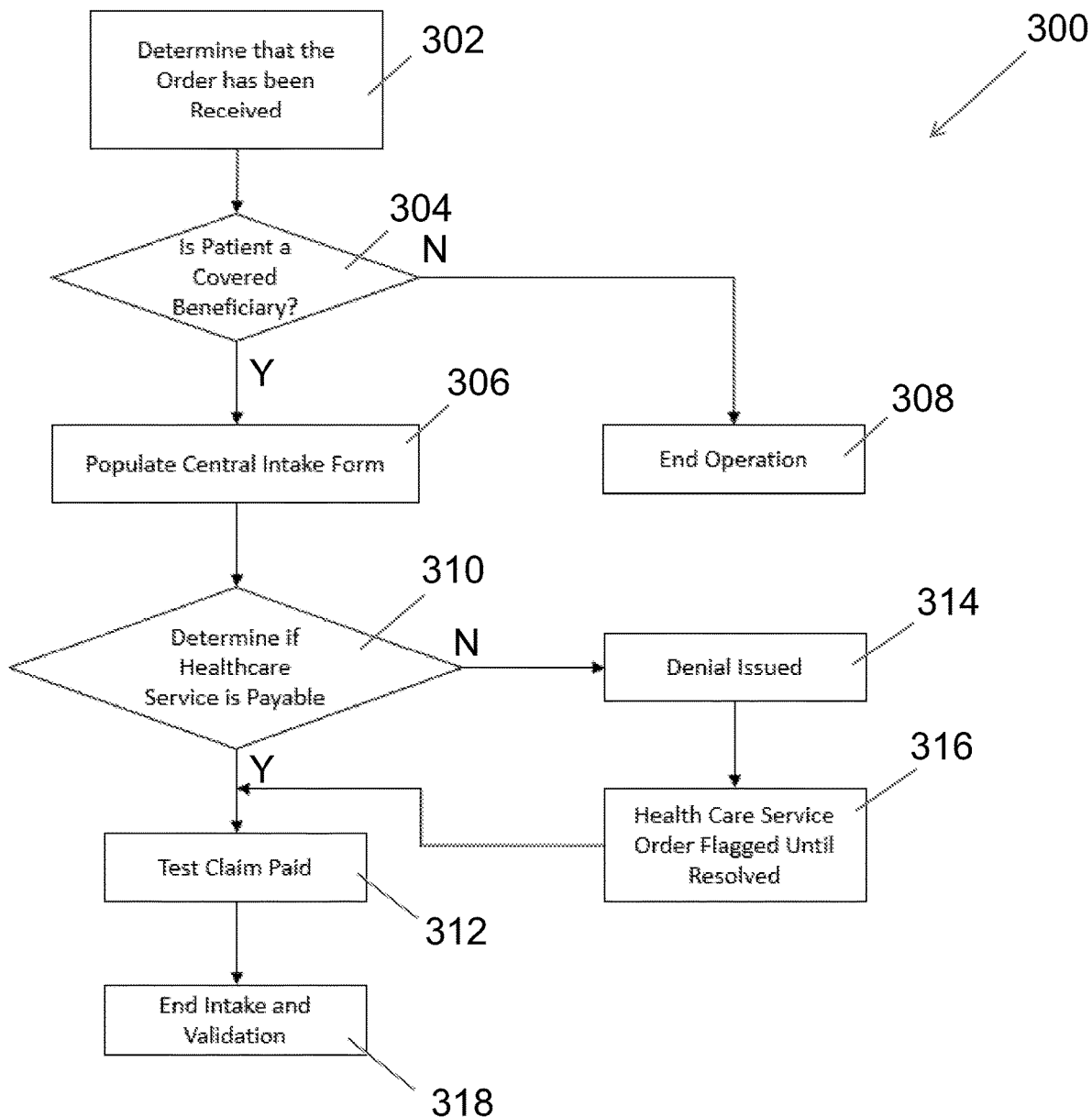
FIG. 3 is a flowchart of an example process for providing an intake and validation procedure according to various embodiments.

The block diagrams of FIGS. 2A-2C illustrate an intake and validation module 128, a patient stratification and bid criteria module 130, and a bidding platform 132. The units or modules shown in FIGS. 2A-2C may include other functions that are not illustrated, but are described in the application. As can be seen in FIG. 2A, the intake and validation module 128 includes an order detector 202, an eligibility verifier 204, a central intake form populator 206, and a claim verifier 208. FIG. 3 is a flowchart of an exemplary process 300 for providing an intake and validation process according to various embodiments. The exemplary process 300 may be performed by, for example, the intake and validation module 128 of FIG. 2A.

In an order receiving operation 302, a healthcare service order is received by the intake and validation module by any available electronic or manual method, such as via facsimile, telephone, through the mail from the U.S. Postal Service or a private parcel service, or via an electronic order, such as an emailed or electronic prescription. If the healthcare service order is received via the U.S. mail or a private parcel service, it will be manually entered into the intake and validation module by an operator. The open healthcare service order may be received from, for example, a claims processor, a provider, such as another specialty pharmacy, a payer, such as an insurance company, directly from a prescriber, such as a doctor's office, or from an intermediary entity such as a hub vendor.

In an eligibility verification operation 304, the eligibility verifier 204 conducts eligibility verification to confirm that a patient is currently a covered beneficiary of a contracted payer (e.g., an insurance company). Preferably, the eligibility verifier 204 connects directly to the payer's own eligibility system in real-time to confirm eligibility. However, if direct connection to the payer's own eligibility system is not possible, the eligibility verifier will either use the payer's online eligibility lookup system, or will attempt to connect to the payer via electronic or telephonic means. If the eligibility verifier determines that a patient is not currently a covered beneficiary of the contracted payer, the intake processing ends in an operation 308.

If the eligibility verifier determines that the patient is currently a covered beneficiary, the healthcare service order moves to a form population operation 306 and the order is captured on a central intake form by the central intake form populator 206. The central intake form is an internal electronic form that contains all legal and payer-specific information that is necessary to proceed with the healthcare service order. The necessary information is either auto-populated on the form or manually entered by an operator. When the central intake form is complete, the healthcare service order is routed to the claim verifier 208.

In a payable determination operation 310, a claim verifier 208 will determine whether the healthcare service order is payable. For example, the claim verifier 208 will run a test claim through a third-party hosted online adjudication system. If the test claim is authorized and is paid (payment step 312), the healthcare service order will proceed to the patient stratification and bid criteria module 130. However, if the test claim is not authorized and is instead denied, the healthcare service order will be flagged. The claim verifier 208 will determine why the denial was issued at step 314, and will attempt to resolve the denial at step 316 in FIG. 3. Once a denied healthcare service order is resolved, the healthcare service order will then proceed to the patient stratification and bid criteria module 130.

Figure 4:
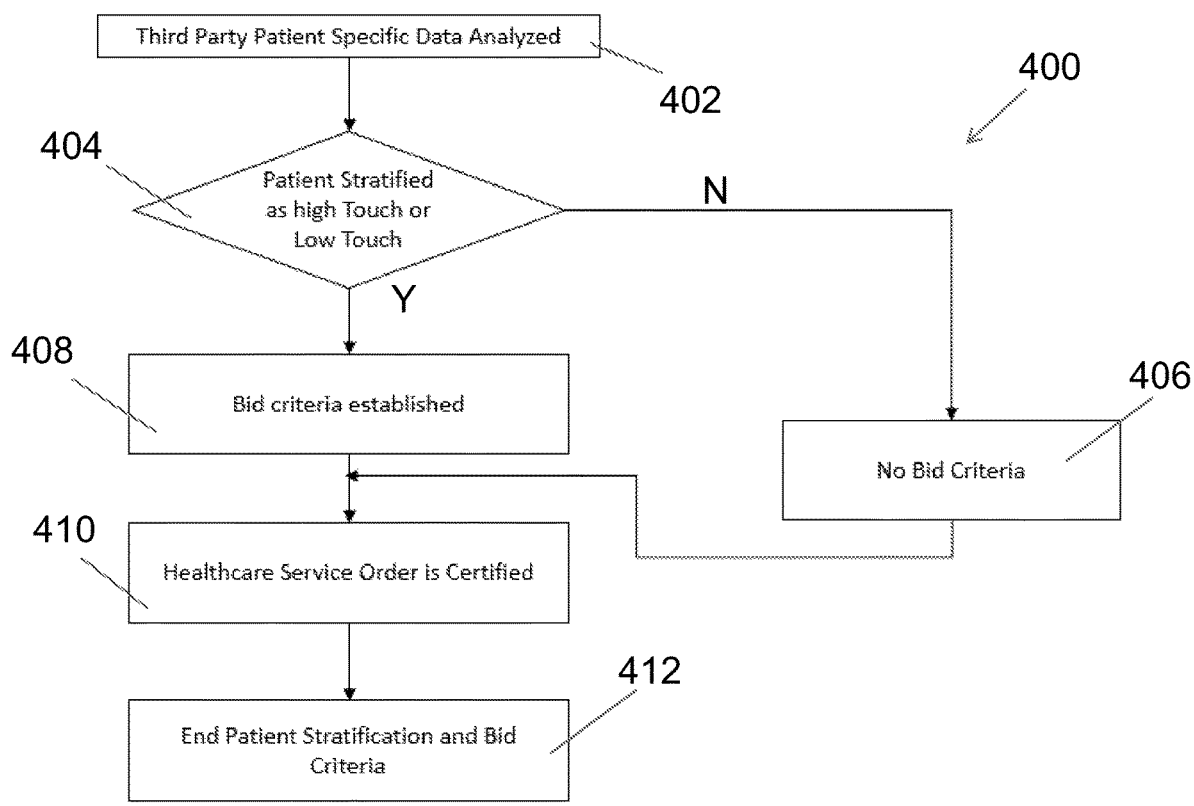
FIG. 4 is a flowchart of an example process for providing a patient stratification and bid criteria procedure according to various embodiments.

FIG. 2B illustrates the patient stratification and bid criteria module 130 that includes a data analyzer 210, a patient stratification unit 212, a bid criteria establishment unit 214, and an order certifier 216. FIG. 4 is a flowchart of an exemplary process 400 for providing a patient stratification and bid criteria according to various embodiments. The exemplary process 400 may be performed by, for example, the patient stratification and bid criteria module of FIG. 2B.

In an operation that preferably occurs at step 402 as shown in FIG. 4, a data analyzer 210 will evaluate patient-specific data from a third party source for characteristics that would qualify the patient for a value-based high touch care model. For example, the data analyzer 210 may look for co-morbid conditions, use of multiple healthcare services, and/or a history of non-compliance to prescribed healthcare services. Based on the outputs of the data analyzer, at step 404 the patient stratification unit 212 will determine, by a pre-defined rule set, whether the patient is in need of a value-based high touch care model or a low touch care model. If the patient stratification unit 212 determines that the healthcare service order requires a value-based high touch care model, the healthcare service order will immediately proceed to step 408 to establish bid criteria for the order. If the patient stratification unit 212 determines that the healthcare service order does not require a value-based high touch care model, at step 406 the healthcare service order proceeds with no bid criteria to be certified at step 410.

At step 408, the bid criteria establishment unit 214 determines the bid criteria that will apply to the healthcare service order when it is finally awarded to a winning service provider. The bid criteria that are established are unique to each particular healthcare service and/or condition that the healthcare service order is servicing. For example, the bid criteria may establish performance metrics that the winning service provider will be measured on to determine if they achieve an incentive payment for that healthcare service order. The bid criteria may also establish an authorization duration. For example, a winning service provider will be assigned an authorization duration of 12 months. Once the bid criteria are established, the healthcare service order is determined to be a certified order at step 410. The patient stratification and bid criteria process ends at step 412. Once the patient stratification and bid criteria process is complete, the certified order is routed to the bidding platform 132.

The processes described above in FIGS. 3 and 4 have the advantage of dramatically reducing the front-end or "pre-work" that a willing provider (for example, a specialty pharmacy) must complete in order to prepare a healthcare service order for fulfillment. In addition, the processes of FIGS. 3 and 4 also have the advantage of reducing a provider's risk that it will not be reimbursed by a payer (for example, an insurance company) for fulfilling the healthcare service order. The reduction of both the front end work and of the reimbursement risk creates an incentive for providers to join and be active within the competitive bidding system. Additionally, the processes described in FIG. 4 enable a value-based network design where healthcare service providers (for example, specialty pharmacies) can receive incentive payments for achieving performance metrics.

Figure 5:
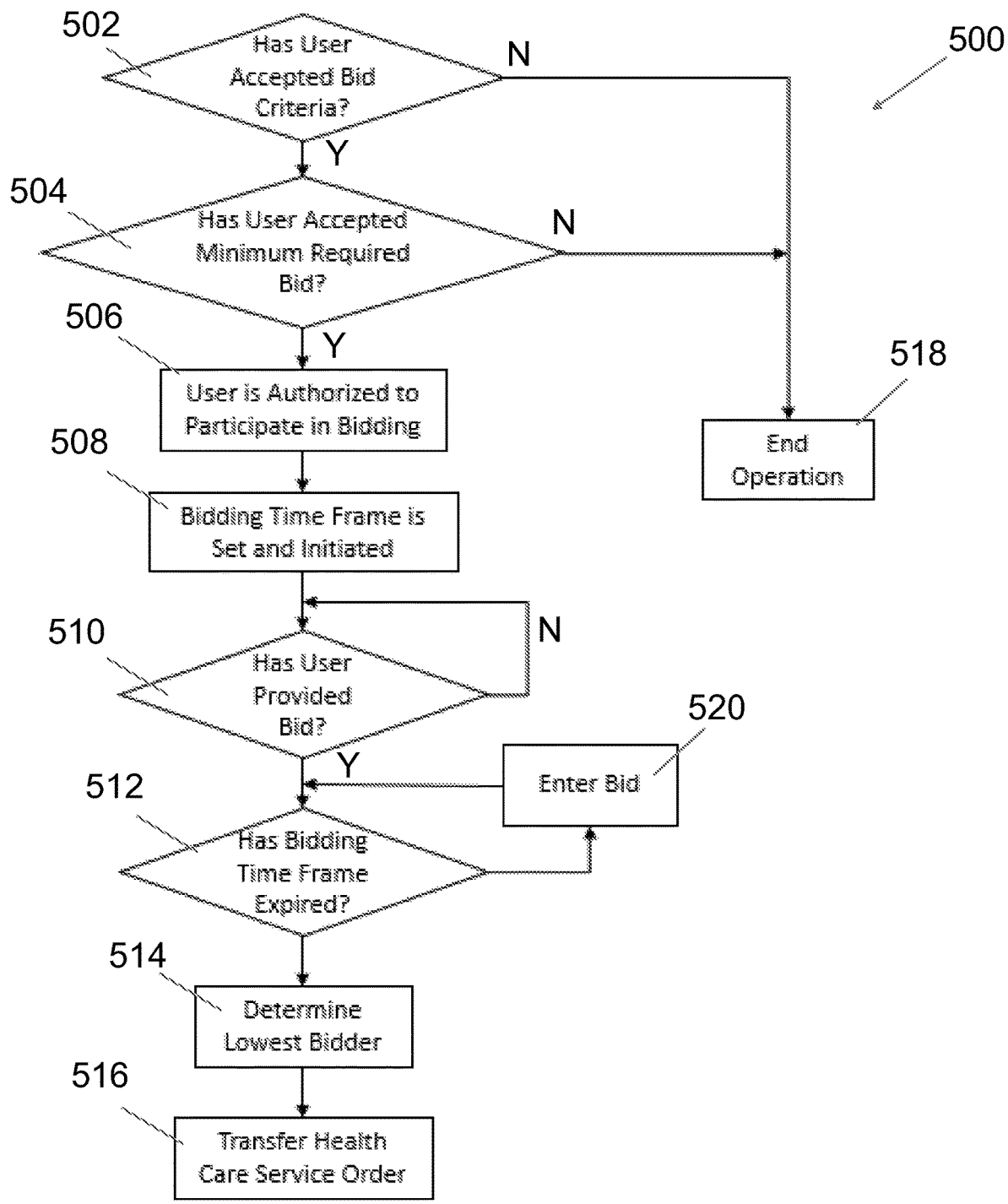
FIG. 5 is a flowchart of an example process for providing a bidding procedure according to various embodiments.

FIG. 2C illustrates the bidding platform 132 that includes a bid manager 218, an authorization unit 220, a time frame manager 222, and an auction manager 224. FIG. 5 is a flowchart of an exemplary process 500 for operation of a bidding platform according to various embodiments. The exemplary process 500 may be performed by, for example, the bidding platform of FIG. 2C.

Once the healthcare service order has been certified by the patient stratification and bid criteria module 130, a user (e.g., a service provider) is able to access the certified healthcare service order via an online competitive bidding platform 132. In order to access the certified healthcare order on the bidding platform, the user must log into the bidding platform using previously determined login credentials. Once the user logs into the online bidding platform, the user may access details about the healthcare service order, and review the requirements for participating in the competitive bidding process. For example, in order to participate in the bidding process, a user may be required, at step 502, to accept all bid criteria that was established by the bid criteria establishment unit 214. If the user does not accept the bid criteria, the operation is ended at step 518 and the user is not authorized to participate in the bidding process. In addition, a user may be required to agree, at step 504, that it is willing to pay a minimum required bid (i.e., the minimum amount that a provider can bid to be awarded a particular healthcare service order). If the user does not accept or agree to the minimum required bid, the operation is ended at step 518 and the user is not authorized to participate in the bidding process. The minimum required bid is determined by the bid manager 218, and is generally the lowest cost value that is acceptable in order for a user to acquire the healthcare service order. Commonly, the minimum required bid will be the default reimbursement rate of a payer (e.g., an insurance company). Once a user has accepted all the requirements, the user is authorized by the authorization unit 220 at step 506 to participate in the bidding.

Next, a bidding time frame is determined by the time frame manager 222 at step 508. For example, a bidding time frame may be set at 3 hours. A service provider provides a bid at step 510. When the bidding time frame expires at step 512, the bidding is closed by the time frame manager 222. Next, at step 514, a winning provider (i.e., the provider submitting the lowest bid that still meets the minimum required bid) is determined by the auction manager 224. At step 516, the order is electronically transferred to the winning user (i.e., the lowest cost service provider) by the auction manager 224. After qualifying orders are fulfilled (for example, orders that contain bid criteria), the service provider will be subject to ongoing performance metric evaluation, as shown in FIG. 7.

The above described process provides a novel business-to-business system and method where an order for a healthcare service is validated, stratified for value-based care, certified as payable, and then made available for bid to the lowest-cost servicing provider. This system and method allows for streamlining of the intake and eligibility verification for the order, and enabling through patient stratification that the right patients get into the right care model. The provision by the bidding system of a certified order provides certainty to prospective providers that they are bidding on a service that will be paid for by the insurance company, and requires little-to-no additional work. In addition, the certainty created by the certified order reduces the labor burden and reimbursement risk for prospective bidding providers. Finally, the open bidding platform creates a market-based price discovery process that yields the real-time best price to fulfill the healthcare service order and manage the patient.

Once bidding is complete and the healthcare service order has been awarded to the winning provider, the winning provider is subject to ongoing performance metric evaluation for orders that contain bid criteria set forth by the bid criteria establishment unit 214.

While the present application discusses the specialty pharmacy market, the system and methods described herein are applicable to any healthcare service in which an order for a healthcare service (i.e., a "referral") is written by a prescriber, requires authorization by a payer, and requires a healthcare service provider to provide the service.

Figure 6:
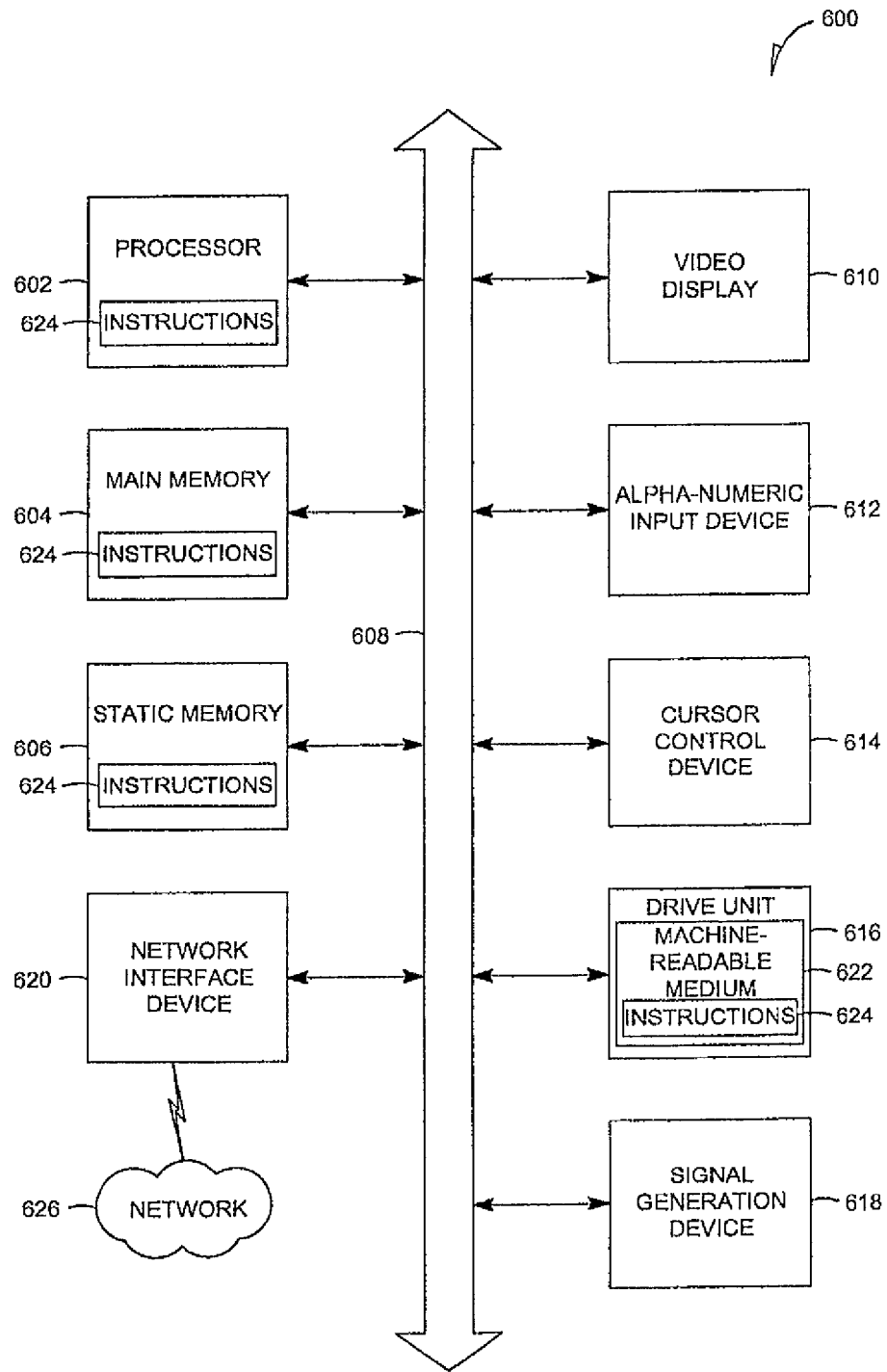
FIG. 6 shows a diagrammatic representation of machine in the example form of a computer system within which a set of instructions, for causing the machine to perform any one or more of the methodologies discussed herein, may be executed.

The exemplary systems and methods disclosed herein may operate utilizing a computer system. FIG. 6, which shows a diagrammatic representation of a machine in the example form of a computer system 600 within which a set of instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 600 includes a processor 602 (e.g., a central processing unit (CPU) a graphics processing unit (GPU) or both), a main memory 604 and a static memory 606, which communicate with each other via a bus 608. The computer system 600 may further include a video display unit 610 (e.g., a liquid crystal display (LCD) or a cathode ray tube (CRT)), The computer system 600 also includes an alphanumeric input device 612 (e.g., a keyboard), a cursor control device 614 (e.g., a mouse), a disk drive unit 616, a signal generation device 618 (e.g., a speaker) and a network interface device 620.

The disk drive unit 616 includes a machine-readable medium 622 on which is stored one or more sets of instructions (e.g., software 624) embodying any one or more of the methodologies or functions described herein. The software 624 may also reside, completely or at least partially, within the main memory 604 and/or within the processor 602 during execution thereof by the computer system 600, the main memory 604 and the processor 602 also constituting machine-readable media. The software 624 may further be transmitted or received over a network 626 via the network interface device 620.

While the machine-readable medium 622 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" should also be taken to include any medium that is capable of storing, encoding or carrying a set of instructions for execution by the machine and that cause the machine to perform any one or more of the methodologies of the present invention. The term "machine-readable medium" shall accordingly be taken to include, but not be limited to, solid-state memories, optical and magnetic media, and carrier wave signals.

FIG. 7 provides a broad overview of the above-described bidding system from intake and validation through ongoing performance metric evaluation. As can be seen from FIG. 7, the bidding system can be divided into the following three "phases:" phase I, which is also known as the stratification & certification phase (which includes the intake and validation process carried out by the intake and validation module 128, and the patient stratification and bid criteria process carried out by the patient stratification and bid criteria module 130); phase II, which is also known as the competitive bidding phase (including the bidding process carried out by the bidding platform 132); and phase III, which is also known as the ongoing performance metric evaluation phase. As described in detail above, in phase I, a healthcare service order that is available for fulfillment arrives in the system via the intake and validation module, then undergoes various intake and validation processes (e.g., eligibility verification, running of a test claim, etc.). After completion of all intake and validation functions, the order proceeds through a patient stratification and bid criteria process. Once the order is stratified and bid criteria established (if applicable), the order is "certified as payable." The certified order then moves through phase II, during which a provider accepts any bid criteria that may have been established and bids on a certified healthcare service order. During phase II, the certified healthcare service order is also awarded to the lowest authorized bidder. In phase III, the winning provider (i.e., the winning bidder) is subject to ongoing evaluation of the performance metrics set forth in the bid criteria.

Certain embodiments are described herein as including logic or a number of components, modules, or mechanisms. Modules (e.g., detector 202 and analyzer 210) may constitute either software modules (e.g., code embodied on a machine-readable medium or in a transmission signal) or hardware modules. A hardware module may be a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation, and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the system and methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

Thus, a method and system to provide a value-based bidding system have been described. Although the present invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

What is claimed is:

1. A healthcare service system comprising:
   an intake and validation module configured to detect and receive a healthcare service order from a buyer, wherein the intake and validation includes a claim verifier configured to determine whether the healthcare service order is payable by performing a payment of a test claim by the buyer;
   a patient stratification and bid criteria module configured to verify the healthcare service order, wherein the patient stratification and bid criteria includes:
      a data analyzer configured to evaluate a patient of the buyer;
      a patient stratification unit configured to determine the patient of the buyer receiving the healthcare service order requires a high touch healthcare service based on the evaluation of the data analyzer;
      a bid criteria establishment unit configured to establish performance metrics for the healthcare service order;
   a bidding platform configured to initiate a reverse bidding process for a plurality of sellers configured to provide the healthcare service order for the patient of the buyer;
   wherein the reverse bidding process creates a winning seller, wherein the winning seller is a lowest bidding seller of the plurality of sellers;
   wherein the winning seller then provides the healthcare service including the requirements determined by the bid criteria establishment unit to the patient of the buyer;
   a performance metric evaluation phase wherein the winning seller is subject to ongoing evaluation of the performance metrics of the healthcare service order set by the bid criteria establishment unit after the patient stratification unit determines that the patient of the healthcare service requires the high touch health care service;
   determining the winning seller has achieved the performance metrics of the healthcare service order set by the bid criteria establishment unit; and
   providing the winning seller with incentive payments for achieving the performance metrics.

2. The health care service system of claim 1, wherein the intake module and validation module further comprises an eligibility verifier, wherein the eligibility verifier confirms the patient of the buyer is eligible for the healthcare service order.

3. The health care service system of claim 1, wherein the intake and validation module further comprises a claim verifier configured to determine whether the healthcare service order is payable.

4. The health care service system of claim 1, wherein the plurality of sellers is required to review and agree to provide the bid criteria and a minimum bid requirement for the reverse bidding process.

5. A method of providing a healthcare service system comprising:
   receiving a healthcare service order from a buyer via an intake module, wherein receiving a healthcare service order includes verifying that the healthcare service order is payable by a claim verifier by performing a payment of a test claim by the buyer;
   verifying the healthcare service order via a patient stratification and bid criteria module, wherein verifying the healthcare service order includes:
      evaluating a patient of the buyer receiving the healthcare order by a data analyzer;
      determining the patient of the buyer receiving the healthcare service order requires a high touch healthcare service based on the evaluation of the data analyzer;
   a reverse bidding process via a bidding platform, wherein the reverse bidding process includes reverse bidding of a plurality of sellers configured to provide the healthcare service order for the patient of the buyer, wherein the reverse bidding process creates a winning seller, wherein the winning seller is a lowest bidding seller of the plurality of sellers;

wherein the winning seller provides the healthcare service order for the patient of the buyer;

monitoring the winning seller in a performance metric evaluation phase, the winning seller is subject to ongoing evaluation of the performance metrics of the healthcare service order set by the bid criteria establishment unit after the patient stratification unit determines that the patient of the healthcare service requires the high touch healthcare service;

determining the winning seller has achieved the performance metrics of the healthcare service order set by the bid criteria establishment unit; and providing the winning seller with incentive payments for achieving the performance metrics.

6. The health care service system of claim 5, wherein the intake module and validation module further comprises an eligibility verifier, wherein the eligibility verifier confirms the patient of the buyer is eligible for the healthcare service order.

7. The health care service system of claim 5, wherein the intake and validation module further comprises a claim verifier configured to determine whether the healthcare service order is payable.

8. The health care service system of claim 5, wherein the plurality of sellers is required to review and agree to provide the bid criteria and a minimum bid requirement for the reverse bidding process.

* * * * *